(12) United States Patent
Spurgeon

(10) Patent No.: US 6,857,328 B1
(45) Date of Patent: Feb. 22, 2005

(54) SAMPLE PROBE FOR AEROSOL SAMPLING APPARATUS

(76) Inventor: Joe C. Spurgeon, 1349 Montevideo Ave., Placentia, CA (US) 92870

( * ) Notice: Subject to any disclaimer, the term of this patent is extended or adjusted under 35 U.S.C. 154(b) by 286 days.

(21) Appl. No.: 10/156,224

(22) Filed: May 23, 2002

(51) Int. Cl.$^7$ .............................................. G01N 1/00
(52) U.S. Cl. ................................ 73/863.21; 73/863.23
(58) Field of Search ....................... 73/863.21, 863.22, 73/863.23, 863.81, 863.33, 863.83, 863.85, 864.73, 864.74, 864.81, 28.01, 28.02, 28.03, 28.04, 28.05, 28.06, 865.5

(56) References Cited

U.S. PATENT DOCUMENTS

| | | | |
|---|---|---|---|
| 5,189,399 A | * | 2/1993 | Beyersdorf ................. 340/629 |
| 5,237,881 A | * | 8/1993 | Ross ...................... 73/863.12 |
| 5,523,744 A | * | 6/1996 | Wieser ....................... 340/630 |
| 5,844,148 A | * | 12/1998 | Klein et al. ............... 73/863.82 |
| 6,408,704 B1 | * | 6/2002 | Willeke ..................... 73/865.5 |

* cited by examiner

*Primary Examiner*—Robert Raevis
(74) *Attorney, Agent, or Firm*—Drummond & Duckworth

(57) ABSTRACT

A sample probe is provided for sampling aerosols within a wall cavity. The sample probe includes a hollow tubular body having a distal end, an intermediate portion, a proximal end and a central passageway. The distal end includes a sharp beveled point provided to inhibit the blockage of a distal open inlet if the distal end is positioned against an object. The probe further includes one or more holes projecting through the probe's tubular body, preferably positioned substantially adjacent to the probe's distal end. The probe further includes a radially projecting region adapted for sealing a hole or opening formed to obtain access to a wall cavity. Moreover, the probe includes a proximal open outlet adapted to connect to the inlet of an aerosol sampling cassette.

2 Claims, 4 Drawing Sheets

SAMPLE PROBE FOR AEROSOL SAMPLING APPARATUS

BACKGROUND OF THE INVENTION

The present invention relates to sampling devices for capturing airborne or liquid-suspended particles. More specifically, the present invention relates to an apparatus for collecting aerosols from wall cavities. As used herein, reference to wall cavities is intended to be given the broadest interpretation including cavities within wall structures, ceiling structures, and the like.

There are numerous prior art filter sampling devices available today. A typical filtration cassette has an inlet and outlet for directing the flow of an initial sample medium, either liquid or gas. Using a vacuum source, gas and/or liquid molecules, as well as particles, are made to pass through the filter medium. The filter medium selectively retains particles based on the particle's size.

An additional conventional air sampling device is commercially available under the trade name, Air-O-Cell®. This air sampler includes a two part cassette having a narrowing inlet and an outlet which is also connected to a vacuum source. Between the two parts of the cassette is a slit directing the air flow onto a 2 mm×14 mm impactor plate having an adhesive on the plate's upper side. In operation, spores, pollen, fibers, etc. enter through the inlet, strike the plate and are adhered to its surface. For analysis, the plate is removed and viewed under a microscope.

Similar to the apparatus described above, European Patent No. 0,129,983 discloses a filter cassette for sampling airborne particles having an inlet, an outlet and a frusto-conically shaped filter medium positioned in between. U.S. Pat. No. 5,437,198 describes a device for separating and capturing airborne particles having a slit nozzle inlet and an internal porous impaction surface. Unimpacted particles follow the airflow past the impaction surface to be either later collected or discharged.

Unfortunately, none of the above described air collection devices, also referred to as sampling cassettes, are suitable for aerosol sampling within a wall cavity. In particular, such cassettes are too large to conveniently fit inside a wall cavity. To overcome this obstacle, a small diameter sample probe is typically attached to the inlet of the cassette, and the sample probe is inserted through a hole in the wall structure into the wall cavity. The aerosols are withdrawn from the wall cavity, passing through the sample probe and into the cassette where it is collected upon an impactor plate or filter medium for analysis.

A commercially available system for collecting airborne aerosols from wall cavities is sold under the tradename WallChek®. The WallChek® system includes a circular hood machined from plastic that fits snugly over the inlet of an aerosol sampling cassette. The WallChek® system further includes a plastic tube of small diameter. The proximal end of the tube is attached to the inlet of the hood and the distal end of the plastic tube is fitted with a plastic or rubber cap. A hole is punched or drilled through the wall and the capped end of the flexible tube is inserted through the hole into the wall cavity. Once inserted, a metal rod is projected through the hole and used to dislodge the protective cap from covering the distal end of the tube. The machined hood is then attached to the inlet of an aerosol sampling cassette. A volume of air is drawn through the cassette by a vacuum source causing sample media to travel through the flexible tube into the sampling cassette.

Unfortunately, the WallChek® device is extremely expensive, costing several hundred dollars. Because of this high cost, the WallChek® assembly is typically reused, with subsequent samples requiring the use of the same hood and flexible tube assembly. This prior art construction is thus susceptible to contamination from prior sampling.

In order to reduce contamination, the hood and flexible tube are typically cleaned between sampling procedures. Unfortunately, this is an often difficult task to perform, particularly when sampling is conducted in the field where cleaning facilities are not available.

An additional disadvantage of the WallChek® system is that the internal diameter of the flexible tube is relatively small causing the tube to be easily clogged by dust and debris generated when the hole is formed in a wall by punching or drilling through drywall or plaster. Though a protective cap is provided when inserting the tube into the wall, the process for removing the cap with a metal rod is cumbersome and time consuming.

Still an additional disadvantage with the prior art wall cavity sample probe is that it uses a thin flexible plastic tube which has only a single opening at the tip of the tube. The opening of the tube is prone to becoming blocked if positioned against a solid object within the wall cavity, such as the wall structure at the rear of the wall cavity. Moreover, if the tube encounters an object within the wall cavity during insertion, the tube is prone to bending sharply, causing crimping of the tube and a reduction in the amount of airflow into the sampling cassette which can effect the integrity of the sample.

It would therefore be advantageous to provide a sample probe for wall cavities which is inexpensive to manufacture, not prone to clogging, and not prone to loss of integrity due to crimping.

It would also be advantageous to provide a wall sample probe in which clogging by dust and debris is not a practical concern.

Furthermore, it would be advantageous to provide an improved wall probe which did not require cleaning between field samples.

SUMMARY OF THE INVENTION

Briefly, and in general terms, the present invention addresses the aforementioned disadvantages by providing an improved sample probe adapted to be inserted into a wall cavity for sampling aerosols. The probe is sufficiently inexpensive to manufacture that it can be replaced between samples so as to be essentially disposable. The difficulties of cleaning, and cross contamination between samples is therefore eliminated. Moreover, the improved wall probe is not prone to crimping, blockage, and the diameter of the probe is sufficiently large so as to eliminate the need for a protective cap and metal rod.

To this end, the wall sampling probe includes a hollow tubular body having a distal open inlet, an intermediate portion, a proximal open outlet and a central passageway extending the length of the tubular body. Of importance, the distal open inlet of the aerosol sampling apparatus is beveled to form a sharp point. The beveled sharp point construction is provided to reduce the propensity of the distal end to become clogged due to the distal end engaging an obstruction, such as the rear portion of the wall. In particular, when positioned against an obstruction, the sharp point of the beveled distal opening engages the obstruction, allowing the withdrawal of air and particulates to tangentially enter the beveled opening.

Meanwhile, the intermediate portion of the probe includes a region having a substantially constant cross section. The region of constant cross section may be cylindrical, or square in cross section, or various other shapes as can be determined by those skilled in the art. For ease of manufacturing, and because it is most simple to form a circular hole in a wall, it is preferred that this region of the probe have a cylindrical construction. Preferably, the probe of the present invention includes one or more holes which project through the cylindrical sidewall to allow the passage of particulates from the exterior of the probe into the probe's central passageway. The probe may have any number of holes. However, in a preferred embodiment, the probe includes a total of six holes, with two sets of three holes located on opposing sides of the probe body. The holes are preferably circular in shape and positioned adjacent to the beveled open inlet.

In a preferred embodiment of the invention, the intermediate portion of the probe includes a frustum shaped region which radially expands from the distal end of the probe towards the proximal end of the probe. The frustum shaped region is located proximal to the holes which project through the intermediate portion of the probe. Where the intermediate portion of the probe is cylindrically shaped, it is preferred that the frustum region be frusto-conically shaped. The frusto-conically shaped region of the probe is provided to seal a hole formed in a wall when the distal end of the probe is projected into such a hole. This is accomplished by projecting the distal end of the probe into the hole until the frusto-conical region engages the wall. Of course as understood by those skilled in the art, the frusto-conical region of the probe must be constructed to have a diameter greater than the diameter of the hole formed in the wall.

Meanwhile, the proximal outlet of the probe is constructed to form an adaptor for attaching to the inlet of an aerosol sampling cassette. The adaptor may take various forms so as to connect to generic or specialized aerosol sampling cassettes, such as 25 mm cassettes, 37 mm cassettes, or cassettes sold under the trade name Air-O-Cell® and Bi-Air®. Moreover, in a preferred embodiment, the adaptor end of the probe is detachable from the remainder of the probe for permitting replacement of the adaptor for adaptors which can mate to alternative cassettes.

To use the sample probe of the present invention, a small hole is formed in the wall structure, such as through drywall, plaster or particle board, to obtain access to the wall cavity undergoing aerosol sampling. The diameter of the hole must be greater than the diameter of the cylindrical intermediate portion of the probe, but smaller than the diameter of the frusto-conically shaped region of the probe. Once the hole has been formed, the distal end of the probe is projected through the hole until the frusto-conical region engages the sidewalls of the hole, thereby sealing the hole except for allowing passage of aerosols through the probe's central passageway. Thereafter, the adaptor forming the proximal region of the probe is connected to an aerosol sampling cassette, which in turn, is connected to a vacuum source. The vacuum source is activated causing the withdrawal of air and aerosols from the wall cavity through the probe's central passageway and into the aerosol sampling cassette so that aerosols are collected on the cassette's impactor plate or filter medium.

It is therefore an object of the present invention to provide for a wall sampling probe which is inexpensive to manufacture, and thus disposable between air sampling procedures. Therefore, the probe eliminates the possibility of cross contamination from previously collected samples, and the elimination of the need to clean the wall probe between samples.

It is an additional object of the invention to provide for a probe which is constructed of a hard, substantially non-deformable material so as not to crimp when being inserted into a wall cavity.

It is still an additional object of the present invention to provide a wall probe which includes a central passageway which is sufficiently large that clogging by dust and debris is not a practical concern and the need for a protective cap and disgorging metal rod is eliminated.

Other features and advantages of the present invention will be appreciated by those skilled in the art upon reading the detailed description which follows with reference to the attached drawings.

DETAILED DESCRIPTION OF THE INVENTION

Figure 1:
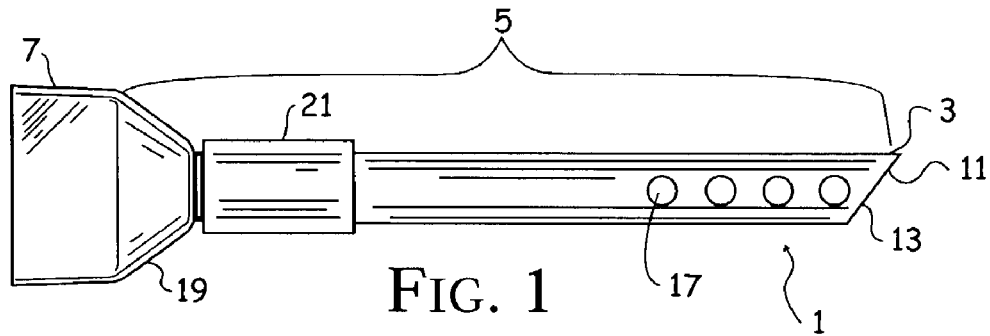
FIG. 1 is a side view of a first embodiment of the sample probe of the present invention.

While the present invention is susceptible of embodiment in various forms, as shown in the drawings, hereinafter will be described the presently preferred embodiments of the invention, with the understanding that the present disclosure is to be considered as an exemplification of the invention, and it is not intended that the invention be limited to the specific embodiments illustrated.

With reference to the figures, and particularly FIGS. 1-4, the sample probe 1 of the present invention includes a distal end 3, an intermediate portion 5, and a proximal end 7. The sample probe 1 is substantially tubular, and thus hollow, forming a central passageway 9 which extends the entire length of the sample probe.

The distal end 3 of the probe includes an open inlet 13 which is beveled forming a sharp point 11. The angle of the bevel may vary greatly as determined by those skilled in the art, depending on various factors such as the material and thickness of the wall, the material being penetrated, and the depth of the wall cavity.

The intermediate portion 5 of the sample probe 1 includes one or more holes 17. The holes are preferably circular and disposed toward the distal end 3 of the sample probe 1. As shown in the figures, four holes are provided for providing passage by aerosols into the probe's central passageway 9. However, the sample probe may include any number of holes, as can be determined by those skilled in the art.

In a preferred embodiment of the invention, the intermediate portion 5 includes a radially projecting region 19 which projects outwardly greater than the diameter of a hole formed in the wall structure. The radially projecting region 19 is preferably positioned proximal to the holes 17 and adjacent to the proximal end 7 of the sample probe. The radially projecting region will typically be frustum shaped. Where the intermediate portion 5 is predominately cylindrically shaped, the radially projecting region 19 will typically be frusto-conically shaped. However, other radially projecting constructions can be determined by those skilled in the art without departing from the spirit and scope of the invention.

Figure 6:
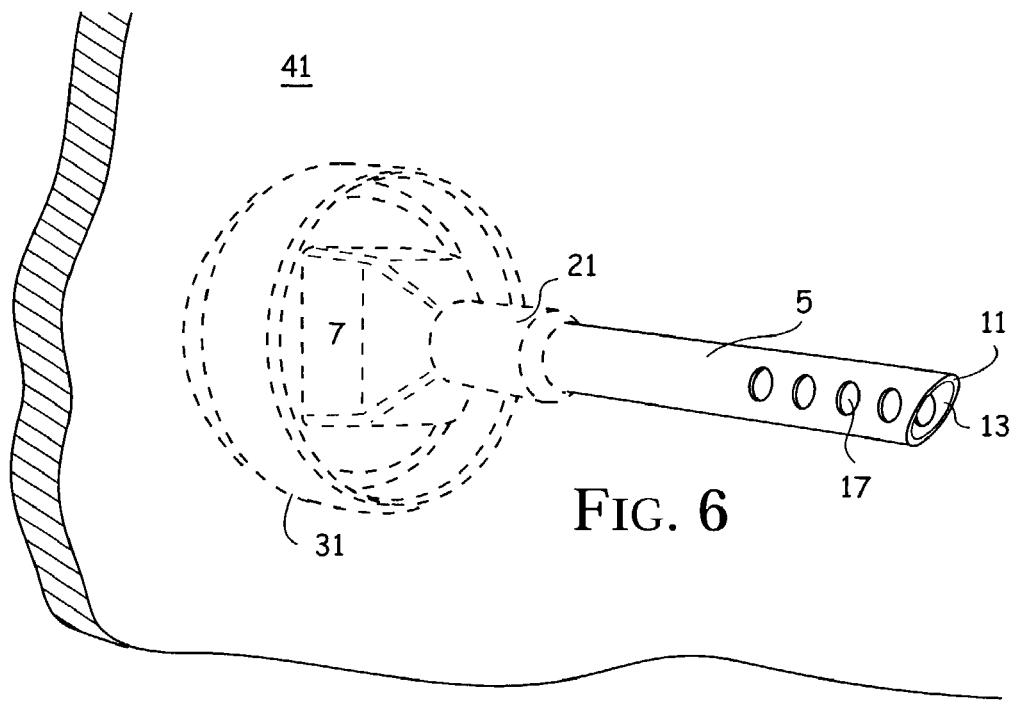
FIG. 6 illustrates a perspective view of the sample probe of the present invention piercing a hole formed in a wall to access a wall cavity.

Adjacent to the intermediate portion 5 of the sample probe is the proximal end 7. The proximal end 7 may be constructed in various forms to mate and engage to the various inlets of specific and generic sampling cassettes, such as 25 mm cassettes, 37 mm cassettes, Air-O-Cell® cassettes and Bi-Air® cassettes. With reference to FIG. 6, the Air-O-Cell® cassette includes a rectangular inlet, and accordingly a sample probe of the present invention intended to mate to an Air-O-Cell® sample cassette is constructed to include a rectangular shaped proximal outlet 15 formed to mate to the Air-O-Cell® cassette by a press-fit engagement. Meanwhile, with reference to FIG. 7, Bi-Air® cassettes typically include a circular inlet, and a sample probe of the present invention intended to mate to such a cassette includes a circular proximal outlet 15, also preferably engaging to the cassette by a press-fit attachment.

Figure 2:
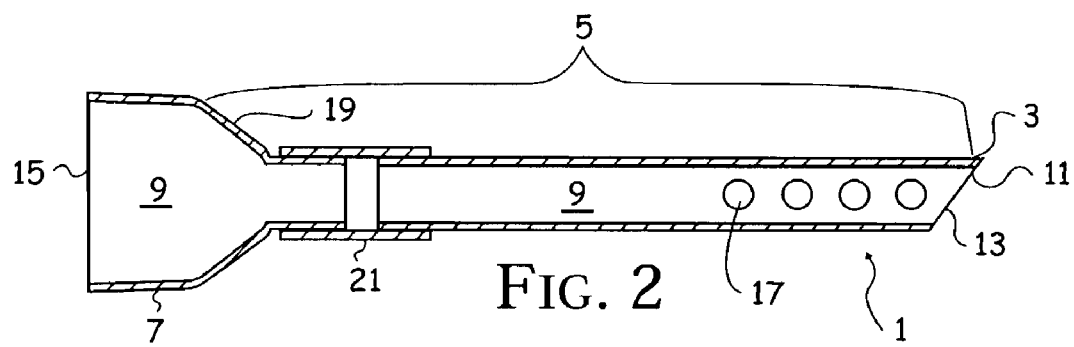
FIG. 2 is a side cross-sectional view of the sample probe of FIG. 1.
Figure 3:
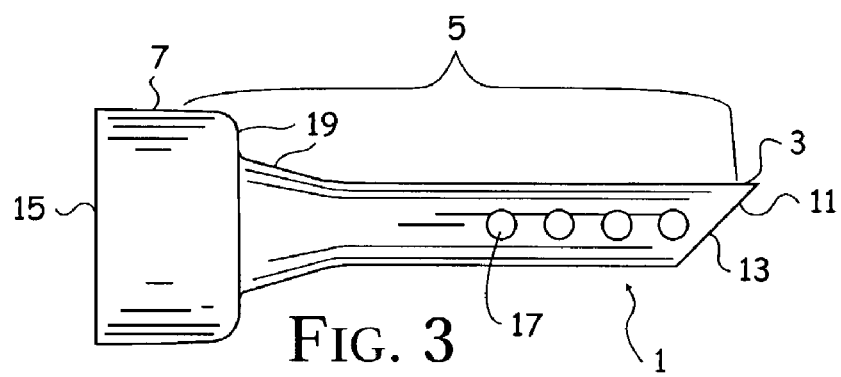
FIG. 3 is a side view of a second embodiment of the sample probe of the present invention.
Figure 4:
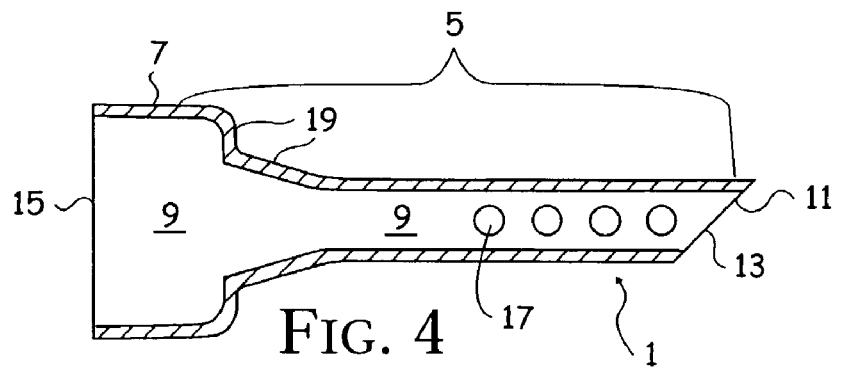
FIG. 4 is a side cross-sectional view of the sample probe of FIG. 3.
Figure 5:
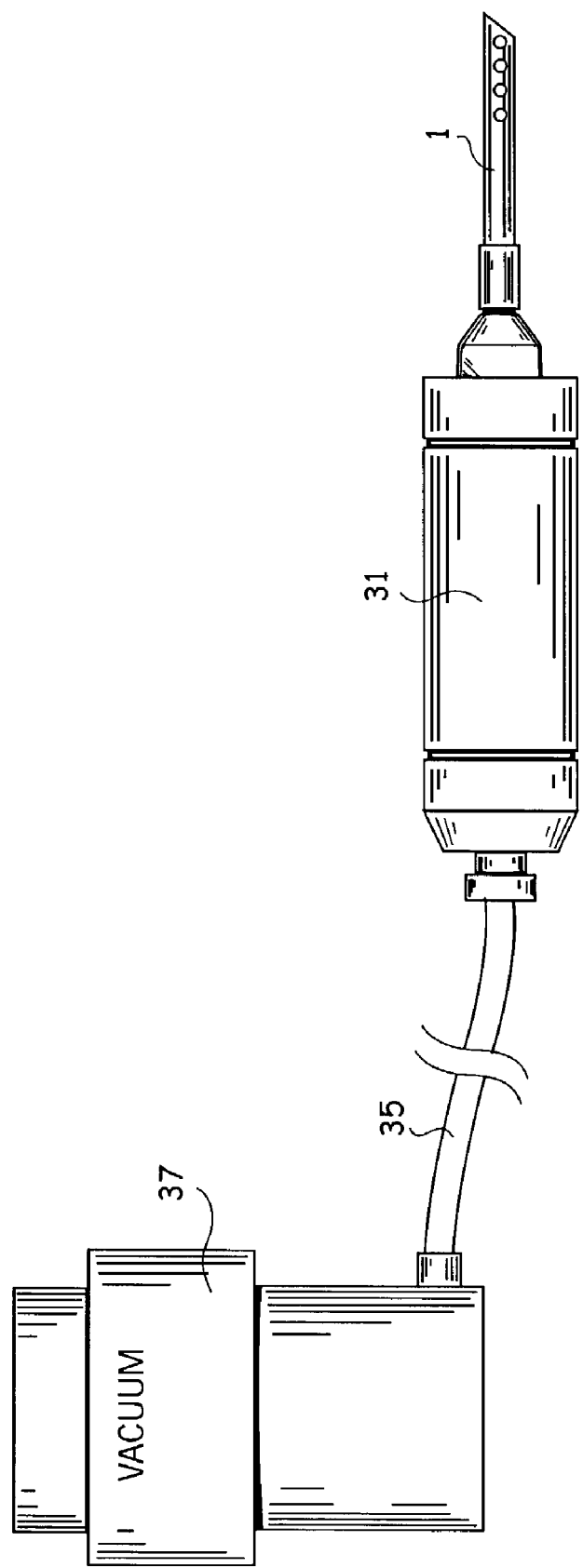
FIG. 5 is a side view illustrating the sample probe of the present invention connected to an aerosol sampling cassette and a vacuum source.

The sample probe 1 may be constructed as one piece, or of multiple components fitted together. For example, as shown in FIGS. 1 and 2, a sample probe 1 is provided wherein the proximal end 7 and radially projecting region 19 is detachable from the remainder of the intermediate portion 5 and distal end 3 of the sample probe. The two pieces are connected by an annular collar 21 which fits snugly over the respective ends to provide an airtight seal. This embodiment provides the advantage that the distal end 3 of the sample probe with its beveled inlet 13 and holes 17, can be fitted with various proximal adaptors 7 for connection to sampling cassettes 31 of various constructions. Conversely, a person using a particular sampling cassette, can fit the cassette with a single adaptor 7 and substitute the remaining portion of the sample probe to alter the length and diameter of the probe, angle of the probe's beveled point 11, or increase the number or size of the holes 17. As would be understood by those skilled in the art, one may wish to change the characteristics of the sample probe depending on factors including the thickness of the wall material and wall cavity, and the aerosols being sampled, among other factors.

The sample probe 1 of the present invention may be constructed of any substantially hard non-porous material, including plastic, metal, ceramic or glass. Preferably, the sample probe is constructed of a static discharging material. As but one example, a preferred material for the construction of the sample probe is carbon filled polypropylene plastic. This material is electrically conductive and allows the static surface charge to dissipate which would otherwise unwantingly attract aerosols during an aerosol sampling procedure. The dimensions of the sample probe may also vary as can be determined by those skilled in the art. For example, the length of the sample probe may be any length that fits within the dimensions of the wall cavity undergoing sampling.

However, for sampling in typical business or residential constructions, a preferred length of the probe is about 50 mm. Again, the outer diameter of the probe may vary, but a preferred outer diameter of the probe towards its distal end is 9 mm. For this construction, it is preferred that the inside diameter of the sample probe be about 6 mm, providing a wall thickness of about 1.5 mm. The holes 17 may be provided in any number, shape or size. However, for the preferred construction of the sample probe, preferably three holes are provided having a diameter of about 3 mm.

Figure 7:
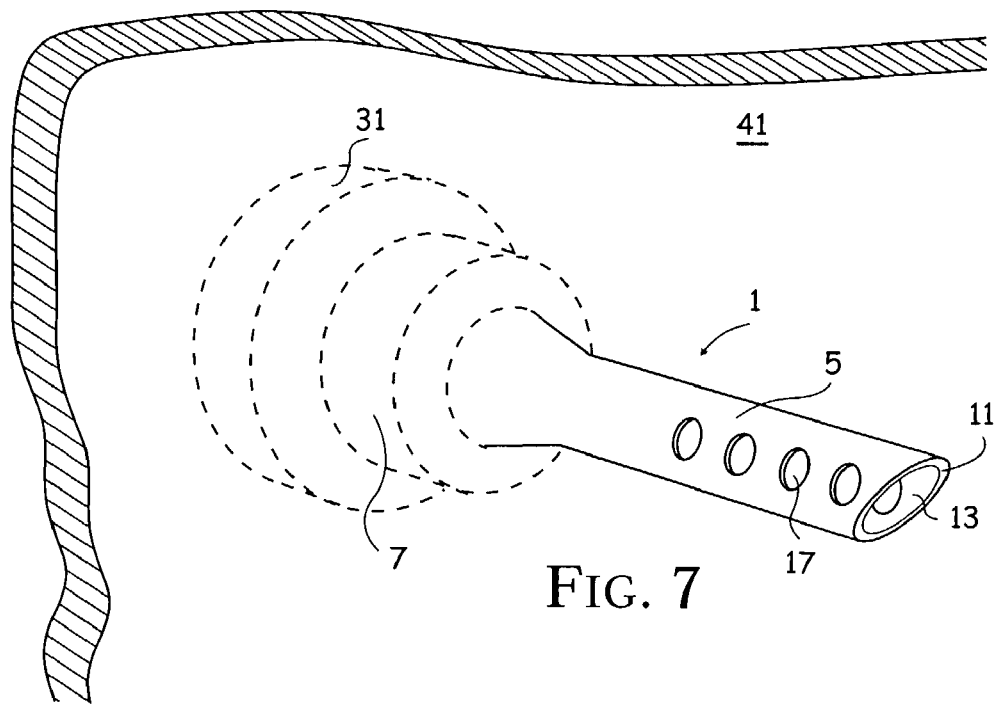
FIG. 7 is a perspective view illustrating a sample probe connected to an aerosol sampling cassette wherein the sample probe is piercing a hole in a wall structure to access a wall cavity.
Figure 8:
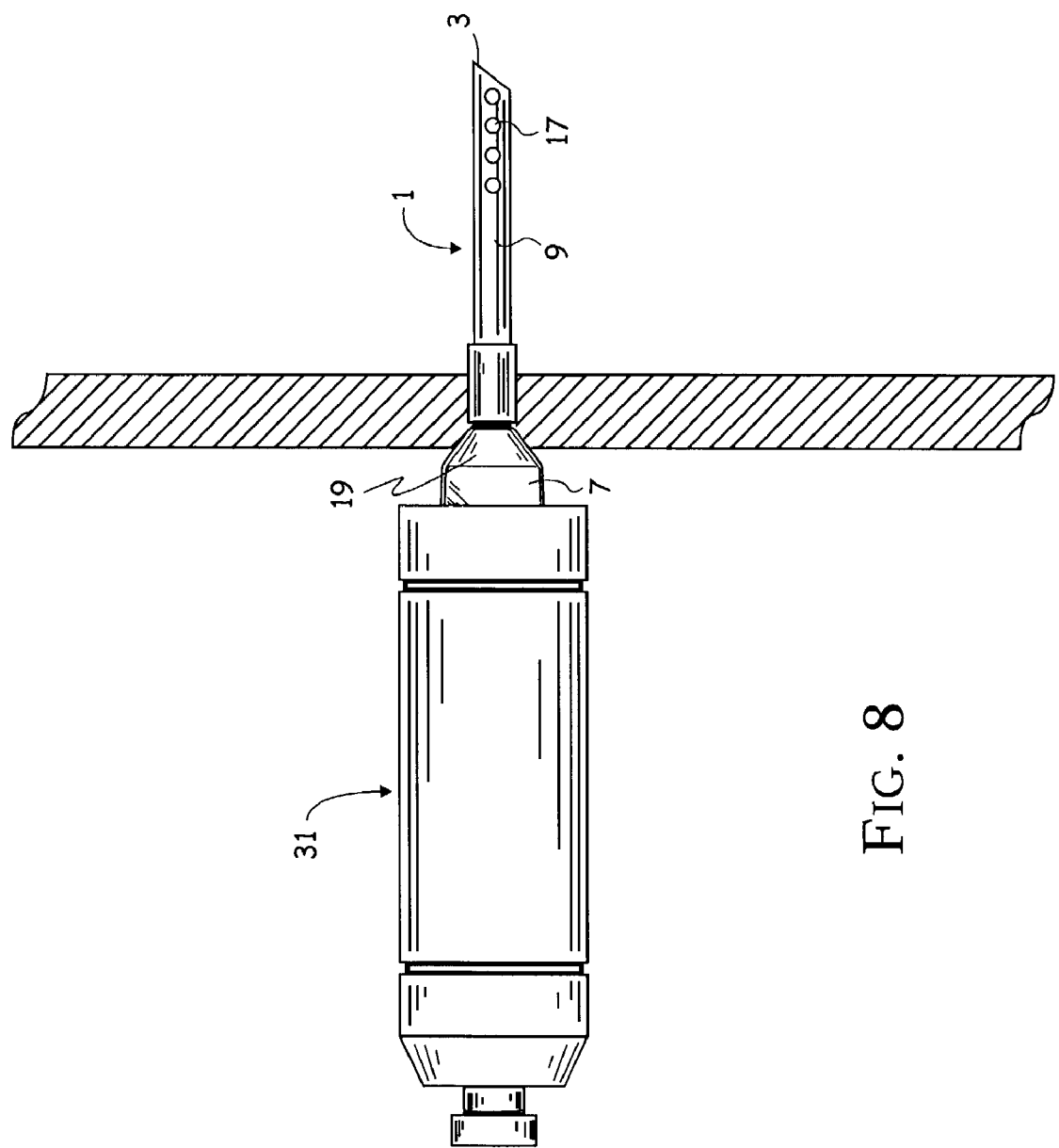
FIG. 8 is a side cross-sectional view illustrating a sample probe connected to an aerosol sampling cassette wherein the sample probe is piercing a hole in a wall structure to access a wall cavity.

With reference to FIGS. 6-8, a preferred method of using the sample probe of the present invention is described as follows. A hole in a wall structure is formed having the same general shape as the cross section of the intermediate portion 5 of the sample probe 1, but having a hole diameter smaller than the outer diameter of the radially projecting region of the sample probe. Thereafter, the distal end of the sample probe is inserted into the hole until the probe's distal inlet 13 and holes 17 are positioned within the wall cavity. Preferably, the sample probe is forced into the hole until the radially projecting region 19 engages the wall structure to form a substantially airtight seal. A sampling cassette is connected to the proximal end of the sample probe. This connection may occur either prior to inserting the sample probe into the wall cavity or thereafter.

Once the sample probe and sampling cassette are in position, a vacuum source connected to the sampling cassette is activated to draw particulates from within the wall cavity through the sample probe to be received and retained by the sampling cassette. The aerosols being collected may be bio-aerosols or environmental contaminants including asbestos and other types of fibers, lead based paint particulates, heavy metals, bacteria, pollen, allergens, and other chemicals.

Other applications and variations of the invention will occur to those skilled in the art. For example, although particular embodiments of the invention have been described herein, it is to be understood that variations may be made in the construction, materials, and shape of the sample probe.

Having described my invention in such term to enable those skilled in the art to make and use it, and having identified the presently preferred embodiments thereof, I claim:

1. An aerosol sampling apparatus for collecting aerosols in liquid or gas comprising:
   a sampling cassette having an inlet port, a body, and an outlet port;
   an aerosol collector positioned within said body of said cassette, said aerosol collector is an impactor plate having an adhesive surface for collecting aerosols; and
   a hollow tubular body having a distal open inlet, an intermediate portion, and a proximal open outlet, said distal open inlet being beveled to form a sharp point to inhibit the blockage of said distal open inlet if the distal end of said tubular body is positioned against an object, said intermediate portion including one or more radially projecting holes for allowing the passage solids, liquids, or gases from the exterior of said tubular body to the interior of said tubular body, said proximal open outlet connected to said inlet of said sampling cassette.

2. An aerosol sampling apparatus for collecting aerosols in liquid or gas comprising:
   a sampling cassette having an inlet port, a body, and an outlet port;
   an aerosol collector positioned within said body of said cassette, said aerosol collector is a filter having a predetermined pore size for allowing the selective passage and collection of aerosols; and a hollow tubular body having a distal open inlet, an intermediate portion, and a proximal open outlet, said distal open inlet being beveled to form a sharp point to inhibit the blockage of said distal open inlet if the distal end of said tubular body is positioned against an object, said intermediate portion including one or more radially projecting holes for allowing the passage solids, liquids, or gases from the exterior of said tubular body to the interior of said tubular body, said proximal open outlet connected to said inlet of said sampling cassette.

* * * * *